(12) United States Patent
Koshino (10) Patent No.: US 12,336,859 B2
(45) Date of Patent: Jun. 24, 2025

(54) DISPLAY DEVICE AND CONTROL METHOD OF DISPLAY DEVICE

(71) Applicant: FUJIFILM Corporation, Tokyo (JP)

(72) Inventor: Riko Koshino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 72 days.

(21) Appl. No.: 18/461,294

(22) Filed: Sep. 5, 2023

(65) Prior Publication Data

US 2023/0404532 A1 Dec. 21, 2023

Related U.S. Application Data

(63) Continuation of application No. PCT/JP2022/006742, filed on Feb. 18, 2022.

(30) Foreign Application Priority Data

Mar. 8, 2021 (JP) .................................. 2021-036485

(51) Int. Cl.
*A61B 8/00* (2006.01)
*A61B 8/08* (2006.01)
*G06F 3/14* (2006.01)

(52) U.S. Cl.
CPC ............ *A61B 8/464* (2013.01); *A61B 8/0825* (2013.01); *A61B 8/463* (2013.01); *G06F 3/1446* (2013.01)

(58) Field of Classification Search
CPC ......... G06T 7/0012; G06T 2207/30004; G06T 2210/41; G06T 2207/10132;
(Continued)

(56) References Cited

U.S. PATENT DOCUMENTS

2005/0171430 A1 8/2005 Zhang et al.
2007/0239006 A1 10/2007 Kamiyama et al.
(Continued)

FOREIGN PATENT DOCUMENTS

JP 2007-236823 A 9/2007
JP 2014-014489 A 1/2014
(Continued)

OTHER PUBLICATIONS

The extended European search report issued by the European Patent Office on Jul. 31, 2024, which corresponds to European Patent Application No. 22766787.0-1122 and is related to U.S. Appl. No. 18/461,294.
(Continued)

*Primary Examiner* — Gerald Johnson
(74) *Attorney, Agent, or Firm* — Studebaker Brackett PLLC (57) ABSTRACT

Provided are a display device and a control method of a display device capable of improving image interpretation efficiency of the user for an ultrasound image. A display device (1) includes: one or a plurality of adjacent monitors (17) that form a single screen; a memory (11) that stores a plurality of display layouts each of which has a plurality of display regions for displaying a plurality of ultrasound images on the single screen; a schematic diagram selection unit (12) that selects, from among a plurality of schematic diagrams each of which divides a breast of a subject under examination into a plurality of regions, one schematic diagram based on a user's designation; a display layout setting unit (13) that sets, on the single screen, a plurality of display regions of a display layout corresponding to the selected schematic diagram; an imaging position reading unit (14) that reads imaging positions from the ultrasound images; and an image disposition unit (15) that disposes the ultra-
(Continued)

sound images in the set display regions based on the read imaging positions.

20 Claims, 7 Drawing Sheets

(58) Field of Classification Search
CPC ... G06T 2219/028; A61B 8/463; A61B 8/465; A61B 8/46; A61B 2576/00
See application file for complete search history.

(56) References Cited

U.S. PATENT DOCUMENTS

| | | | |
|---|---|---|---|
| 2007/0274585 A1* | 11/2007 | Zhang | G16H 30/20 382/132 |
| 2010/0022881 A1 | 1/2010 | Fujita et al. | |
| 2012/0014578 A1 | 1/2012 | Karssemeijer et al. | |
| 2015/0139518 A1 | 5/2015 | Oohashi et al. | |
| 2015/0146855 A1 | 5/2015 | Futamura | |
| 2017/0100098 A1 | 4/2017 | Urabe et al. | |
| 2018/0028146 A1 | 2/2018 | Zhang et al. | |
| 2018/0301216 A1* | 10/2018 | Nakamura | G06F 16/51 |
| 2019/0378314 A1* | 12/2019 | Umezawa | A61B 8/4416 |
| 2021/0085285 A1 | 3/2021 | Fukuda et al. | |

FOREIGN PATENT DOCUMENTS

| | | |
|---|---|---|
| JP | 2015-100661 A | 6/2015 |
| JP | 2017-070608 A | 4/2017 |
| JP | 2018-027298 A | 2/2018 |
| WO | 2019/190798 A1 | 10/2019 |

OTHER PUBLICATIONS

International Search Report issued in PCT/JP2022/006742; mailed Apr. 12, 2022.
International Preliminary Report On Patentability (Chapter I) and Written Opinion of the International Searching Authority issued in PCT/JP2022/006742; issued Sep. 12, 2023.

* cited by examiner

DISPLAY DEVICE AND CONTROL METHOD OF DISPLAY DEVICE

CROSS-REFERENCE TO RELATED APPLICATIONS

This application is a Continuation of PCT International Application No. PCT/JP2022/006742 filed on Feb. 18, 2022, which claims priority under 35 U.S.C. § 119(a) to Japanese Patent Application No. 2021-036485 filed on Mar. 8, 2021. The above applications are hereby expressly incorporated by reference, in their entirety, into the present application.

BACKGROUND OF THE INVENTION

1. Field of the Invention

The present invention relates to a display device that is used for image interpretation of an ultrasound image and a control method of a display device.

2. Description of the Related Art

Conventionally, an ultrasound image representing a tomogram of a subject under examination has been captured using an ultrasound diagnostic apparatus, and the subject under examination has been diagnosed based on the captured ultrasound image. During such diagnosis, a user such as a doctor may interpret a plurality of frames of ultrasound images displayed on a display device. In order to improve the image interpretation efficiency of the user, a technique has been developed to classify and sort the plurality of frames of ultrasound images, as disclosed in, for example, JP2015-100661A. In JP2015-100661A, in a case where a so-called brightness mode (B-mode) image and a color Doppler image regarding a breast of a subject under examination are captured as ultrasound images, a plurality of frames of ultrasound images are classified into the B-mode image and the color Doppler image, and ultrasound images are sorted and displayed based on the classification.

SUMMARY OF THE INVENTION

However, in a case of examining the breast of the subject under examination, ultrasound images are usually captured at a plurality of imaging positions. Therefore, even in a case of using the technique disclosed in JP2015-100661A, the user still needs to make an effort to determine which imaging position each of the plurality of ultrasound images obtained by the examination corresponds to, which poses a problem that the image interpretation efficiency of the user may be lowered.

The present invention has been made in order to solve such a conventional problem, and an object of the present invention is to provide a display device and a control method of a display device capable of improving the image interpretation efficiency of the user for ultrasound images.

In order to achieve the above-described object, according to the present invention, there is provided a display device comprising: one or a plurality of adjacent monitors that form a single screen; a memory that stores a plurality of display layouts each of which has a plurality of display regions for displaying a plurality of ultrasound images on the single screen; a schematic diagram selection unit that selects, from among a plurality of schematic diagrams each of which divides a breast of a subject under examination into a plurality of regions, one schematic diagram based on a user's designation; a display layout setting unit that sets, on the single screen, a plurality of display regions of a display layout corresponding to the schematic diagram selected by the schematic diagram selection unit; an imaging position reading unit that reads imaging positions of the ultrasound images from the ultrasound images; and an image disposition unit that disposes the ultrasound images in the display regions set by the display layout setting unit, based on the imaging positions read by the imaging position reading unit.

The display layout setting unit may set, on the single screen, a plurality of display regions disposed at positions corresponding to a plurality of regions in the schematic diagram selected by the schematic diagram selection unit.

In addition, the display layout setting unit may change the plurality of display regions already set on the single screen, based on the user's instruction.

In the display device, a finding determination unit that determines presence or absence of a finding in the ultrasound image may further be provided, and the display layout setting unit may set, on the single screen, a plurality of display regions of different display layouts depending on a case where the finding determination unit determines the presence of the finding and a case where the finding determination unit determines the absence of the finding.

Further, the display layout setting unit may set, on the single screen, a plurality of display regions for arranging and displaying an ultrasound image captured in a latest examination performed on the same subject under examination and an ultrasound image captured in a past examination, based on the user's instruction.

Further, the display layout setting unit may also set, on the single screen, a plurality of display regions for arranging and displaying an ultrasound image captured in an examination performed on the same subject under examination and an examination image acquired in an examination other than an ultrasound examination, based on the user's instruction.

Further, the display layout setting unit may set, among a plurality of display regions corresponding to both left and right breasts of the subject under examination, a plurality of display regions corresponding to one breast based on the imaging positions read by the imaging position reading unit or the user's instruction, and sets a plurality of display regions corresponding to the other breast by reversing disposition of imaging positions corresponding to the set plurality of display regions.

Further, the display layout setting unit may set, on the single screen, a plurality of display regions for arranging and displaying a B-mode image and a color image captured in an ultrasound examination performed on the same subject under examination, based on the user's instruction.

The imaging position reading unit may read the imaging position of the ultrasound image by analyzing a schema image that is superimposed and displayed on the ultrasound image and that indicates a position of an ultrasound probe during imaging with respect to the breast.

The imaging position reading unit may also read the imaging position of the ultrasound image based on a position of an ultrasound probe, which is written in a tag accompanying the ultrasound image.

According to the present invention, there is provided a control method of a display device, comprising: causing a memory to store a plurality of display layouts each of which has a plurality of display regions for displaying a plurality of ultrasound images on a single screen formed by one or a plurality of adjacent monitors; selecting, from among a plurality of schematic diagrams each of which divides a breast of a subject under examination into a plurality of regions, one schematic diagram based on a user's designation; setting, on the single screen, a plurality of display regions of a display layout corresponding to the selected schematic diagram; reading imaging positions of the ultrasound images from the ultrasound images; and disposing the ultrasound images in the set display regions based on the read imaging positions.

In the control method of a display device, a plurality of display regions disposed at positions corresponding to a plurality of regions in the schematic diagram selected based on the user's designation may be set on the single screen.

In addition, in the control method of a display device, the plurality of display regions already set on the single screen may be changed based on the user's instruction.

Further, in the control method of a display device, determining presence or absence of a finding in the ultrasound image may further be provided, and a plurality of display regions of different display layouts depending on a case where the presence of the finding is determined and a case where the absence of the finding is determined may be set on the single screen.

Further, in the control method of a display device, a plurality of display regions for arranging and displaying an ultrasound image captured in a latest examination performed on the same subject under examination and an ultrasound image captured in a past examination may be set on the single screen based on the user's instruction.

Further, in the control method of a display device, a plurality of display regions for arranging and displaying an ultrasound image captured in an examination performed on the same subject under examination and an examination image acquired in an examination other than an ultrasound examination may also be set on the single screen based on the user's instruction.

Further, in the control method of a display device, among a plurality of display regions corresponding to both left and right breasts of the subject under examination, a plurality of display regions corresponding to one breast may be set based on the read imaging positions or the user's instruction, and a plurality of display regions corresponding to the other breast may be set by reversing disposition of imaging positions corresponding to the set plurality of display regions.

Further, in the control method of a display device, a plurality of display regions for arranging and displaying a B-mode image and a color image captured in an ultrasound examination performed on the same subject under examination may be set on the single screen based on the user's instruction.

Further, in the control method of a display device, the imaging position of the ultrasound image may be read by analyzing a schema image that is superimposed and displayed on the ultrasound image and that indicates a position of an ultrasound probe during imaging with respect to the breast.

Further, in the control method of a display device, the imaging position of the ultrasound image may also be read based on a position of an ultrasound probe, which is written in a tag accompanying the ultrasound image.

According to the present invention, the display device comprises: one or a plurality of adjacent monitors that form a single screen; a memory that stores a plurality of display layouts each of which has a plurality of display regions for displaying a plurality of ultrasound images on the single screen; a schematic diagram selection unit that selects, from among a plurality of schematic diagrams each of which divides a breast of a subject under examination into a plurality of regions, one schematic diagram based on a user's designation; a display layout setting unit that sets, on the single screen, a plurality of display regions of a display layout corresponding to the schematic diagram selected by the schematic diagram selection unit; an imaging position reading unit that reads imaging positions of the ultrasound images from the ultrasound images; and an image disposition unit that disposes the ultrasound images in the display regions set by the display layout setting unit, based on the imaging positions read by the imaging position reading unit. Therefore, it is possible to improve the image interpretation efficiency of the user for the ultrasound image.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
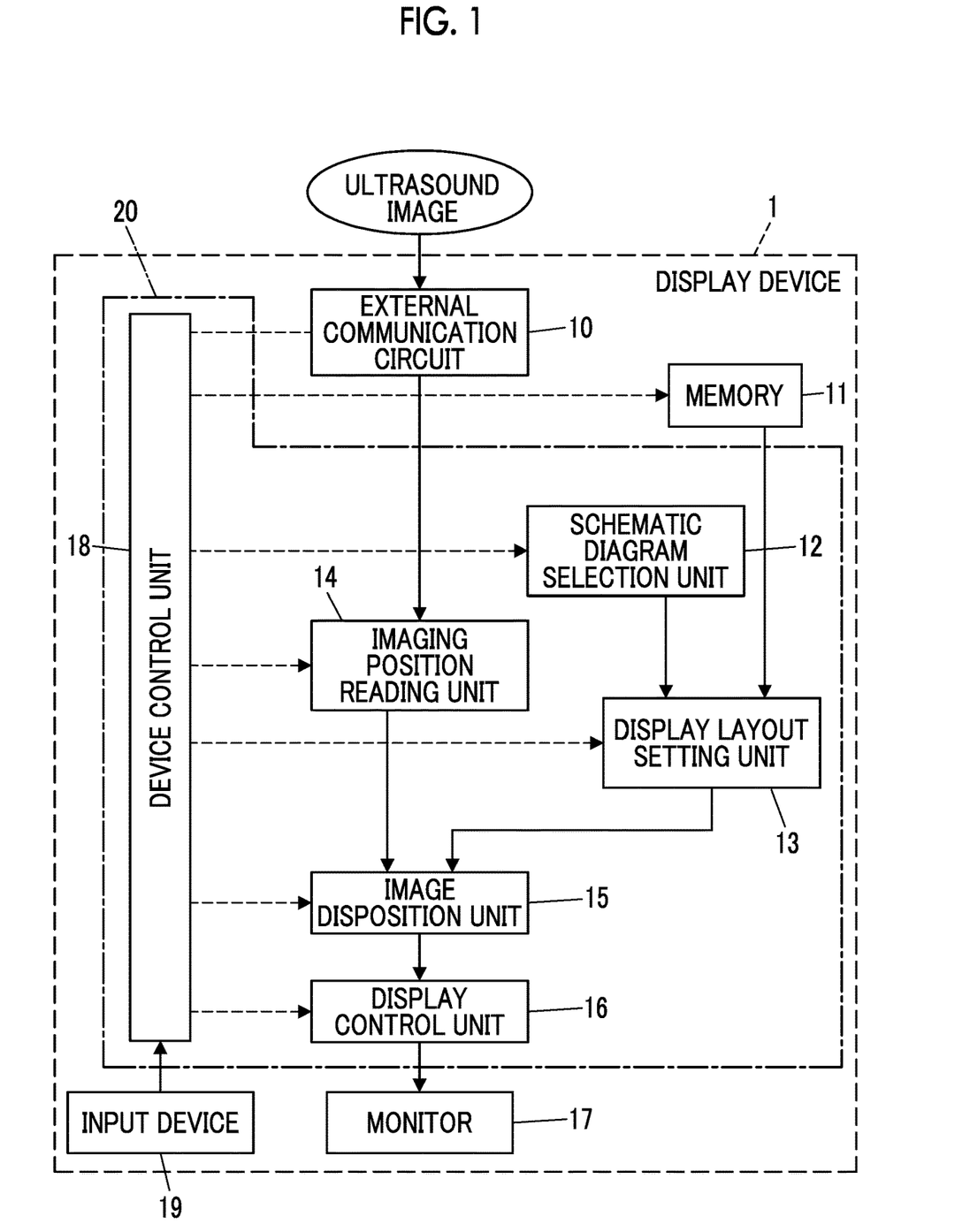
FIG. 1 is a block diagram showing a configuration of a display device according to Embodiment 1 of the present invention.

FIG. 1 shows a configuration of a display device 1 according to Embodiment 1 of the present invention. The display device 1 comprises a memory 11 and a schematic diagram selection unit 12, and a display layout setting unit 13 is connected to the memory 11 and the schematic diagram selection unit 12. In addition, the display device 1 comprises an external communication circuit 10 to be connected to an external device (not shown), and an imaging position reading unit 14 is connected to the external communication circuit 10. In addition, an image disposition unit 15 is connected to the display layout setting unit 13 and the imaging position reading unit 14. Further, a display control unit 16 and a monitor 17 are sequentially connected to the image disposition unit 15.

Further, a device control unit 18 is connected to the external communication circuit 10, the memory 11, the schematic diagram selection unit 12, the display layout setting unit 13, the imaging position reading unit 14, the image disposition unit 15, and the display control unit 16. Further, an input device 19 is connected to the device control unit 18.

In addition, a processor 20 for the display device 1 is composed of the schematic diagram selection unit 12, the display layout setting unit 13, the imaging position reading unit 14, the image disposition unit 15, the display control unit 16, and the device control unit 18.

The display device 1 receives an ultrasound image from an external ultrasound diagnostic apparatus (not shown), a server device (not shown), or the like and is used for a user to interpret the received ultrasound image.

The memory 11 stores a plurality of display layouts each of which has a plurality of display regions for displaying a plurality of ultrasound images on a single screen of the monitor 17, respectively.

Figure 2:
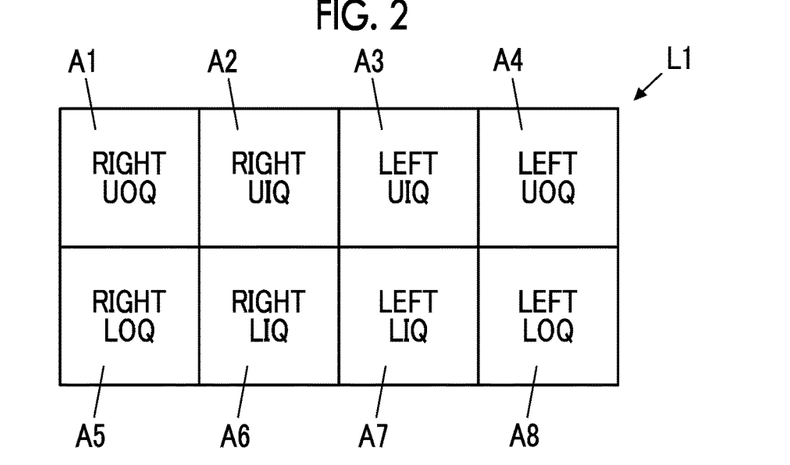
FIG. 2 is a diagram showing an example of a display layout in Embodiment 1 of the present invention.

For example, as shown in FIG. 2, a display layout L1 has eight display regions A1 to A8 for displaying the ultrasound images. Among the eight display regions A1 to A8, four display regions A1, A2, A5, and A6 located on a left side correspond to regions in which a right breast of a subject under examination in a case where the right breast is viewed from the front is divided into four regions centered on a nipple. More specifically, the display region A1 corresponds to a so-called upper outer quadrant (UOQ), which refers to an upper and outer region centered on the nipple, the display region A2 corresponds to a so-called upper inner quadrant (UIQ), which refers to an upper and inner region centered on the nipple, the display region A5 corresponds to a so-called lower outer quadrant (LOQ), which refers to a lower and outer region centered on the nipple, and the display region A6 corresponds to a so-called lower inner quadrant (LIQ), which refers to a lower and inner region centered on the nipple.

Among the eight display regions A1 to A8, four display regions A3, A4, A7, and A8 located on a right side correspond to regions in which a left-side breast of the subject under examination in a case where the left breast is viewed from the front is divided into four regions centered on the nipple. More specifically, the display region A3 corresponds to the UIQ, the display region A4 corresponds to the UOQ, the display region A7 corresponds to the LIQ, and the display region A8 corresponds to the LOQ.

Here, in order to clearly indicate imaging positions of the breast in examining the breast of the subject under examination, a plurality of schematic diagrams each of which divides the breast of the subject under examination into a plurality of regions are known. For example, schematic diagrams are known, such as a schematic diagram which divides each of the left and right breasts of the subject under examination into four regions centered on the nipple, that is, the UOQ, the UIQ, the LOQ, and the LIQ, a schematic diagram which divides each of the left and right breasts of the subject under examination into a center region where the nipple is located and regions corresponding to directions of 1 o'clock to 12 o'clock on a clock and centered on the nipple, and a schematic diagram which divides each of the left and right breasts of the subject under examination into concentric circles centered on the nipple in a case where the left and right breasts are viewed from the front and into a plurality of contour lines with the nipple as the top in a case where the left and right breasts are viewed from the side.

The memory 11 stores a plurality of display layouts corresponding to a plurality of breast schematic diagrams, that is, a plurality of display layouts each of which has a plurality of display regions corresponding to breast regions divided in each of the plurality of breast schematic diagrams.

As the memory 11, for example, recording media, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), can be used.

The schematic diagram selection unit 12 selects one of a plurality of types of schematic diagrams of the breast of the subject under examination based on the user's designation made via the input device 19. Information on the selected schematic diagram is transmitted to the display layout setting unit 13.

The display layout setting unit 13 sets, among the plurality of display layouts stored in the memory 11, a plurality of display regions of a display layout corresponding to the schematic diagram selected by the schematic diagram selection unit 12, as a display layout in a case of displaying the ultrasound images on the single screen of the monitor 17. Information on the plurality of display regions set by the display layout setting unit 13 is transmitted to the image disposition unit 15.

Under the control of the device control unit 18, the external communication circuit 10 communicates with an external device, such as an external ultrasound diagnostic apparatus, a storage device, or a server device (not shown), and acquires the ultrasound images from the external device. The external communication circuit 10 can perform so-called wired communication or wireless communication with the external device (not shown).

Figure 3:
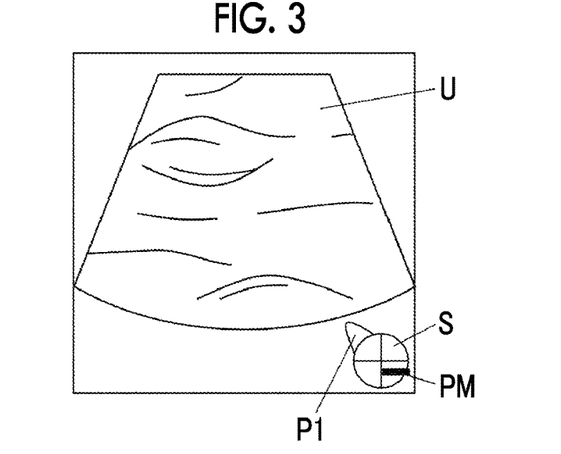
FIG. 3 is a diagram showing an example of an ultrasound image displayed on a monitor in Embodiment 1 of the present invention.

The imaging position reading unit 14 reads the imaging positions of the ultrasound images in the breast from the ultrasound images acquired by the external communication circuit 10. The imaging position reading unit 14 acquires an ultrasound image U as shown in FIG. 3, for example. A so-called schema image S for indicating the imaging position in the breast of the subject under examination is superimposed on the ultrasound image U, and a probe mark PM indicating a position of an ultrasound probe in a case where the ultrasound image U is captured is disposed in the schema image S. In the schema image S of FIG. 3, a protrusion P1 represents the imaging position of the right-side breast of the subject under examination because the protrusion P1 representing a side portion of the subject under examination is disposed on the left side of the circular figure.

The imaging position reading unit 14 can read the imaging position of the ultrasound image U by, for example, performing image analysis on the schema image S in which the probe mark PM is disposed, to recognize at which position on the schema image S the probe mark PM is disposed.

Further, in a case where information regarding the imaging position is stored in a DICOM tag of the ultrasound image U, the imaging position reading unit 14 can also read the imaging position of the ultrasound image U by reading the information stored in the DICOM tag.

The image disposition unit 15 automatically disposes the ultrasound images in the plurality of display regions set by the display layout setting unit 13 based on the imaging positions read by the imaging position reading unit 14 and displays the ultrasound images disposed in the plurality of display regions on the monitor 17.

Figure 4:
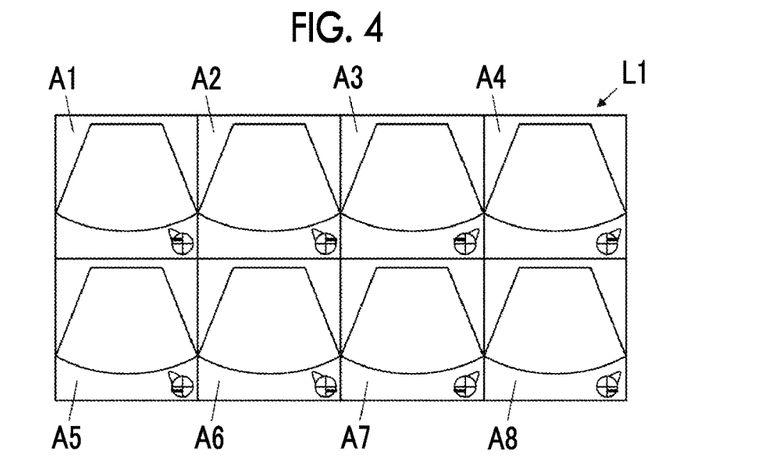
FIG. 4 is a diagram showing an example in which ultrasound images are disposed in display regions of the display layout in Embodiment 1 of the present invention.

For example, in a case where the eight display regions A1 to A8 of the display layout L1 shown in FIG. 2 are set by the display layout setting unit 13, ultrasound images captured at imaging positions corresponding to the eight display regions A1 to A8 are disposed as shown in FIG. 4, respectively. That is, an ultrasound image captured at the UOQ imaging position of the right breast is disposed in the display region A1, an ultrasound image captured at the UIQ imaging position of the right breast is disposed in the display region A2, an ultrasound image captured at the LOQ imaging position of the right breast is disposed in the display region A5, and an ultrasound image captured at the LIQ imaging position of the right breast is disposed in the display region A6. In addition, an ultrasound image captured at the UIQ imaging position of the left breast is disposed in the display region A3, an ultrasound image captured at the UOQ imaging position of the left breast is disposed in the display region A4, an ultrasound image captured at the LIQ imaging position of the left breast is disposed in the display region A7, and an ultrasound image captured at the LOQ imaging position of the left breast is disposed in the display region A8.

The device control unit 18 controls each unit of the display device 1 in accordance with a program recorded in advance or the like.

Under the control of the device control unit 18, the display control unit 16 performs predetermined processing on the ultrasound image or the like and displays the ultrasound image on the monitor 17.

The monitor 17 performs various kinds of display under the control of the display control unit 16. The monitor 17 includes, for example, a display device such as a liquid crystal display (LCD) or an organic electroluminescence (EL) display.

The input device 19 is used for the user to perform an input operation. The input device 19 is composed of, for example, a device that is used for the user to perform an input operation, such as a keyboard, a mouse, a track ball, a touch pad, or a touch panel.

The processor 20 including the schematic diagram selection unit 12, the display layout setting unit 13, the imaging position reading unit 14, the image disposition unit 15, the display control unit 16, and the device control unit 18 is composed of a central processing unit (CPU) and a control program for causing the CPU to perform various kinds of processing, but the processor may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the schematic diagram selection unit 12, the display layout setting unit 13, the imaging position reading unit 14, the image disposition unit 15, the display control unit 16, and the device control unit 18 of the processor 20 can also be configured by being integrated partially or entirely into one CPU or the like.

Next, the operation of the display device 1 according to Embodiment 1 of the present invention will be described with reference to the flowchart shown in FIG. 5.

In step S1, in a case where one of the plurality of types of schematic diagrams representing the breast of the subject under examination is designated by the user via the input device 19, the schematic diagram selection unit 12 selects the schematic diagram designated by the user. For example, although not shown, a list of the plurality of types of schematic diagrams is displayed on the monitor 17, and the user can designate one of the plurality of types of schematic diagrams in the list via the input device 19. The information on the schematic diagram selected in this manner is transmitted to the display layout setting unit 13.

Next, in step S2, the display layout setting unit 13 sets, among the plurality of display layouts stored in the memory 11, a plurality of display regions of a display layout corresponding to the type of schematic diagram selected in step S1, on the single screen of the monitor 17. For example, in a case where a type of schematic diagram in which the left and right breasts of the subject under examination are each divided into four regions centered on the nipple is selected in step S1, the display layout setting unit 13 can set the eight display regions A1 to A8 of the display layout L1 on the single screen of the monitor 17 as shown in FIG. 2.

The display layout L1 has the four display regions A1, A2, A5, and A6 corresponding to four imaging positions, that is, the UOQ, the UIQ, the LOQ, and the LIQ of the right-side breast of the subject under examination, and the four display regions A3, A4, A7, and A8 corresponding to four imaging positions, that is, the UIQ, the UOQ, the LIQ and the LOQ of the left-side breast of the subject under examination.

In this way, since the display layout setting unit 13 sets a plurality of display regions of the display layout corresponding to the breast schematic diagram on the single screen of the monitor 17, the ultrasound images are displayed in the set plurality of display regions. In such a case, the user can intuitively and easily grasp which ultrasound image corresponds to the imaging position.

In step S3, the imaging position reading unit 14 acquires the ultrasound image U as shown in FIG. 3 from the external ultrasound diagnostic apparatus (not shown), the external server device (not shown), or the like via the external communication circuit 10.

Subsequently, in step S4, the imaging position reading unit 14 reads the imaging position of the ultrasound image U from the ultrasound image U acquired in step S3. The imaging position reading unit 14 can read the imaging position of the ultrasound image U by, for example, performing image analysis on the schema image S in which the probe mark PM is disposed, to recognize at which position on the schema image S the probe mark PM is disposed. Further, in a case where information regarding the imaging position is stored in the DICOM tag of the ultrasound image U, the imaging position reading unit 14 can also read the imaging position of the ultrasound image U by reading the information stored in the DICOM tag.

In step S5, the image disposition unit 15 disposes the ultrasound images in display regions corresponding to the imaging positions as shown in FIG. 4 based on the display layout set in step S2 and the imaging positions of the ultrasound images read in step S4. In the example of FIG. 4, in the eight display regions A1 to A8 of the display layout L1 shown in FIG. 2, the ultrasound images captured at the corresponding imaging positions are disposed, respectively.

In this way, in the plurality of display regions A1 to A8 of the set display layout L1, the ultrasound images captured at the corresponding imaging positions are automatically disposed, respectively, so that the user can eliminate the effort to dispose the ultrasound images, and the user can efficiently interpret the ultrasound images.

Finally, in step S6, the image disposition unit 15 causes the monitor 17 to display the ultrasound images disposed in the eight display regions A1 to A8 of the display layout L1 in step S5.

Figure 5:
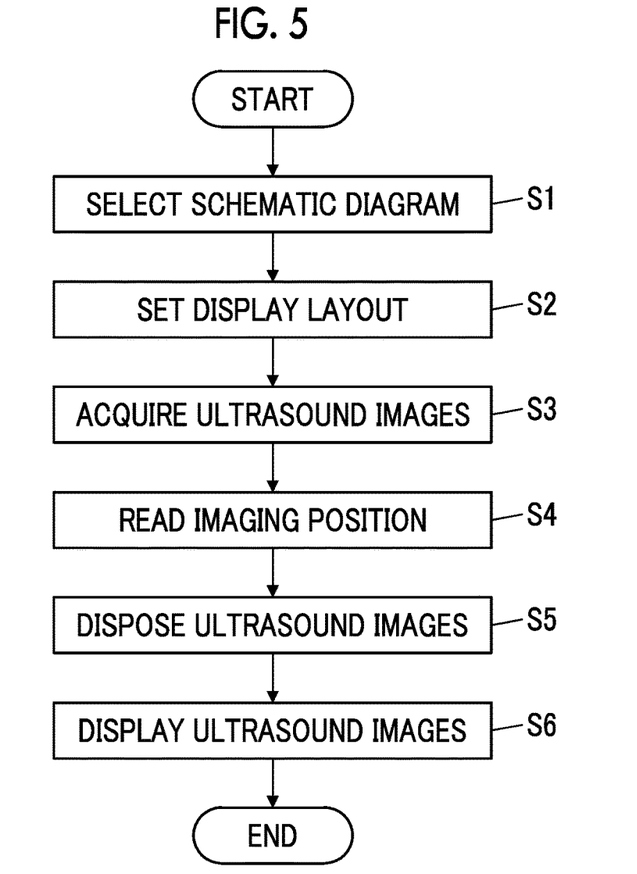
FIG. 5 is a flowchart showing an operation of the display device according to Embodiment 1 of the present invention.

With that, the operation of the display device 1 according to the flowchart of FIG. 5 ends.

From the above, with the display device 1 according to Embodiment 1 of the present invention, the display layout corresponding to the breast schematic diagram designated by the user is automatically set, the imaging positions are read from the ultrasound images, and the ultrasound images are automatically disposed in the display layout based on the imaging positions and displayed on the monitor 17, so that the user can intuitively grasp where the ultrasound image corresponding to which imaging position is disposed, and the image interpretation efficiency for the ultrasound image can be improved.

In addition, since the ultrasound images captured at the imaging positions corresponding to the plurality of display regions of the display layout are automatically disposed, the user can eliminate the effort to dispose the ultrasound images in accordance with the display layout, which makes it possible to improve the image interpretation efficiency.

Figure 6:
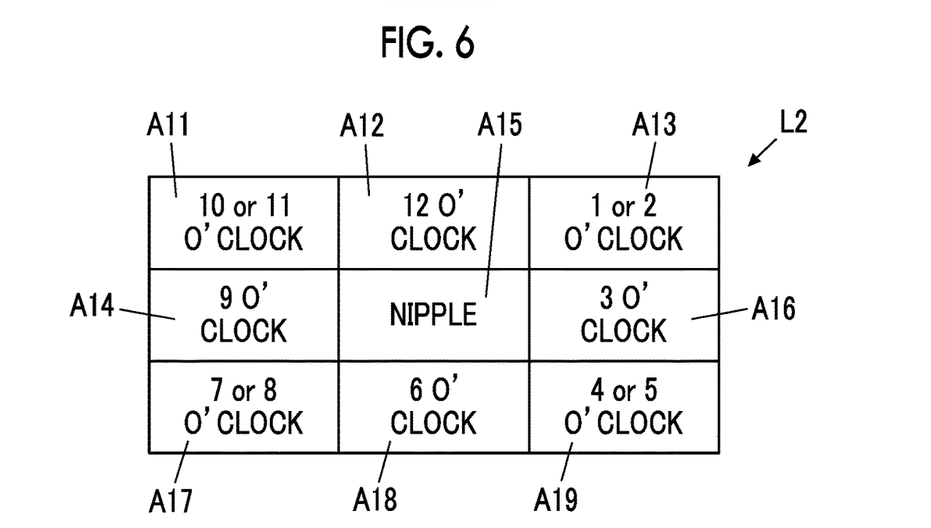
FIG. 6 is a diagram showing another example of the display layout in Embodiment 1 of the present invention.

Although the display layout L1 as shown in FIG. 2 is described, examples of the display layout stored in the memory 11 also include a display layout L2 as shown in FIG. 6, which corresponds to the schematic diagram that divides each of the left and right breasts of the subject under examination into the center region where the nipple is located and regions corresponding to the directions of 1 o'clock to 12 o'clock on the clock and centered on the nipple. The display layout L2 has nine display regions A11 to A19. The display region A11 is a region corresponding to 10 o'clock or 11 o'clock on the clock, the display region A12 is a region corresponding to 12 o'clock on the clock, the display region A13 is a region corresponding to 1 o'clock or 2 o'clock on the clock, the display region A14 is a region corresponding to 9 o'clock on the clock, the display region A15 is the center region where the nipple is located, the display region A16 is a region corresponding to 3 o'clock on the clock, the display region A17 is a region corresponding to 7 o'clock or 8 o'clock on the clock, the display region A18 is a region corresponding to 6 o'clock on the clock, and the display region A19 is a region corresponding to 4 o'clock or 5 o'clock on the clock.

In addition to the above, although not shown, the memory 11 stores a plurality of display layouts corresponding schematic diagrams, such as a schematic diagram which divides each of the left and right breasts of the subject under examination into concentric circles centered on the nipple in a case where the left and right breasts are each viewed from the front and into a plurality of contour lines with the nipple as the top in a case where the left and right breasts are each viewed from the side. Therefore, it is possible to set a display layout in conformity with the user's purpose, preference, or the like.

Figure 7:
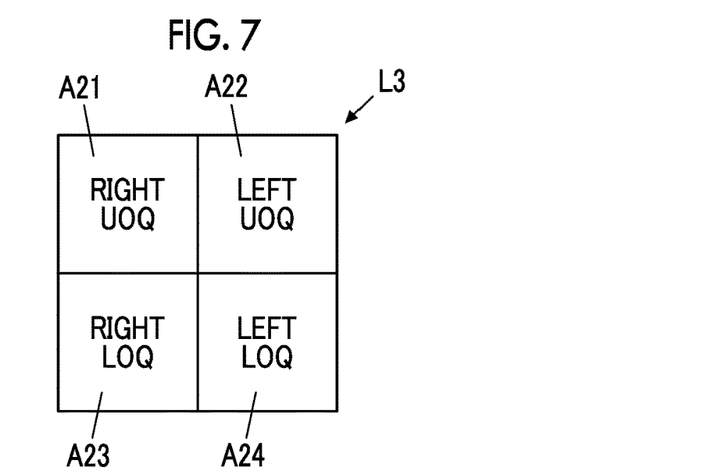
FIG. 7 is a diagram showing an example of a display layout set by a user in Embodiment 1 of the present invention.

In addition, the display layout setting unit 13 can change the plurality of display regions already set on the single screen of the monitor 17 based on an input operation of the user via the input device 19. In this case, the display layout setting unit 13 can set, for example, the number of display regions included in the display layout, a disposition position of the display region corresponding to each imaging position, a degree of magnification of the ultrasound image disposed in the display region, and the like, based on a designation from the user. For example, in a case where the schematic diagram selection unit 12 selects a schematic diagram which divides each of the left and right breasts of the subject under examination into four regions and the user designates the number of display regions of the display layout to four, the display layout setting unit 13 can set a display layout L3 having four display regions A21 to A24, as shown in FIG. 7. The display region A21 of the display layout L3 corresponds to the UOQ imaging position of the right breast, the display region A22 corresponds to the UOQ imaging position of the left breast, the display region A23 corresponds to the LOQ imaging position of the right breast, and the display region A24 corresponds to the LOQ imaging position of the left breast.

Figure 8:
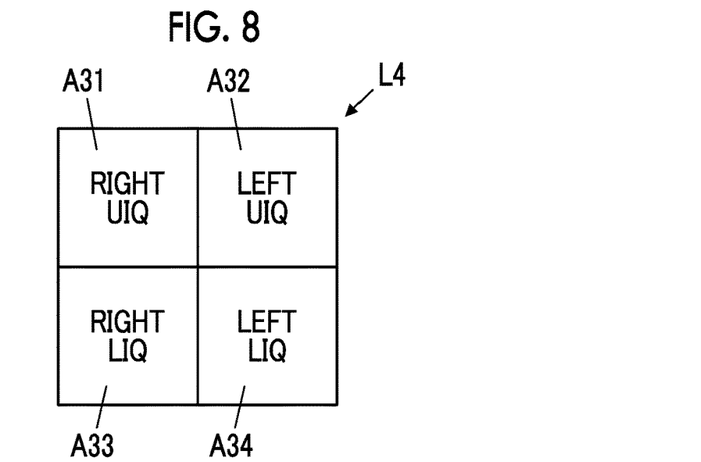
FIG. 8 is a diagram showing another example of the display layout set by the user in Embodiment 1 of the present invention.

In addition, the display layout setting unit 13 can also set, for example, four display regions A31 to A34 of a display layout L4 as shown in FIG. 8 on the single screen of the monitor 17. The display region A31 corresponds to the UIQ imaging position of the right breast, the display region A32 corresponds to the UIQ imaging position of the left breast, and the display region A33 corresponds to the LIQ imaging position of the right breast, and the display region A34 corresponds to the LIQ imaging position of the left breast.

In addition, the display layout setting unit 13 can also set, for example, each of the display regions A21 to A24 of the display layout L3 and the display regions A31 to A34 of the display layout L4 on the single screen of the monitor 17. In such a case, for example, after the ultrasound images disposed in the display regions A21 to A24 of the display layout L3 are displayed on the monitor 17, the ultrasound images disposed in the display regions A31 to A34 of the display layout L4 may be displayed on the monitor 17 in response to an instruction from the user via the input device 19. In this case, the user can diagnose the subject under examination by interpreting in order the ultrasound images disposed in the display regions A21 to A24 of the display layout L3 and the ultrasound images displayed in the display regions A31 to A34 of the display layout L4.

Figure 9:
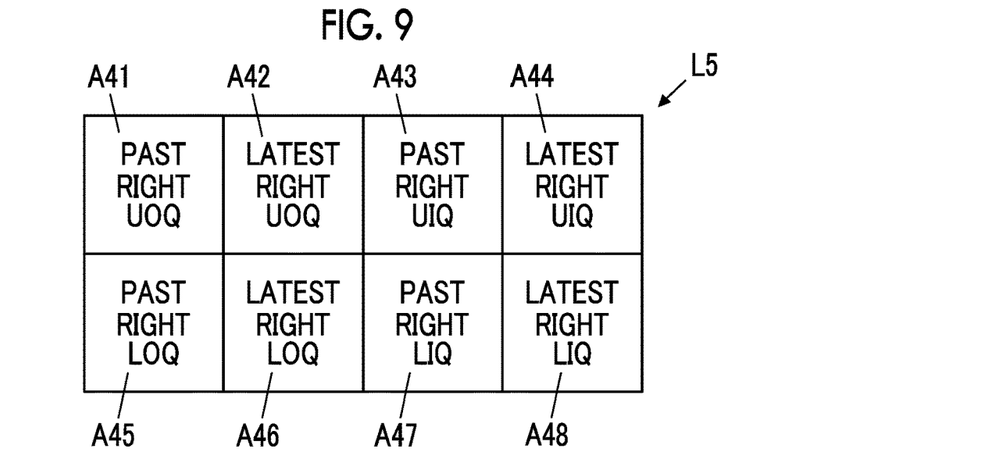
FIG. 9 is a diagram showing an example of a display layout in which an ultrasound image captured in a latest examination and an ultrasound image captured in a past examination are displayed together in Embodiment 1 of the present invention.

Further, for example, as shown in FIG. 9, the display layout setting unit 13 can also set, on the single screen of the monitor 17, eight display regions A41 to A48 of a display layout L5 for displaying ultrasound images captured in a latest examination of the subject under examination and ultrasound images captured in a past examination of the same subject under examination. The display region A41 corresponds to the UOQ imaging position of the right breast imaged in the past examination, the display region A42 corresponds to the UOQ imaging position of the right breast imaged in the latest examination, the display region A43 corresponds to the UIQ imaging position of the right breast imaged in the past examination, the display region A44 corresponds to the UIQ imaging position of the right breast imaged in the latest examination, the display region A45 corresponds to the LOQ imaging position of the right breast imaged in the past examination, the display region A46 corresponds to the LOQ imaging position of the right breast imaged in the latest examination, the display region A47 corresponds to the LIQ imaging position of the right breast imaged in the past examination, and the display region A48 corresponds to the LIQ imaging position of the right breast imaged in the latest examination.

The display layout setting unit 13 can set the date and time of the past examination in which the ultrasound images disposed in the display layout L5 are captured, the imaging positions of the ultrasound images displayed in the display regions A41 to A48 of the display layout L5, and the like based on an input operation of the user via the input device 19.

In this way, a plurality of display regions for displaying the ultrasound image captured in the latest examination and the ultrasound image captured in the past examination of the same subject under examination are set on the single screen of the monitor 17, so that the user can easily compare the latest examination result of the subject under examination with the past examination result, and the image interpretation efficiency of the ultrasound image can be improved.

Figure 10:
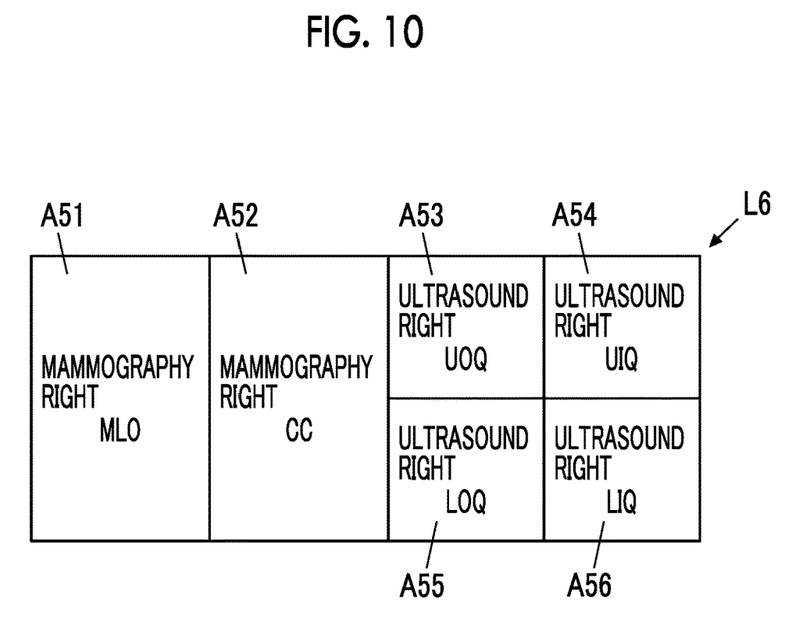
FIG. 10 is a diagram showing an example of a display layout in which a mammography image and an ultrasound image are displayed together in Embodiment 1 of the present invention.

Further, for example, as shown in FIG. 10, the display layout setting unit 13 can set, on the single screen of the monitor 17, six display regions A51 to A56 of a display layout L6 for displaying ultrasound images captured in an ultrasound examination and examination images captured in an examination other than the ultrasound examination on the single screen of the monitor 17. The display regions A51 to A56 of FIG. 10 are regions for arranging and displaying so-called mammography images and ultrasound images on the single screen.

The display region A51 corresponds to a mammography image captured at a so-called medio-lateral-oblique (MLO) imaging position of the right breast, the display region A52 corresponds to a mammography image captured at a so-called cranio-caudal (CC) imaging position of the right breast, the display region A53 corresponds to the ultrasound image captured at the UOQ imaging position of the right breast, the display region A54 corresponds to the ultrasound image captured at the UIQ imaging position of the right breast, the display region A55 corresponds to the ultrasound image captured at the LOQ imaging position of the right breast, and the display region A56 corresponds to the ultrasound image captured at the LIQ imaging position of the right breast.

The display layout setting unit 13 can set a display layout for displaying a so-called magnetic resonance imaging (MRI) image or a so-called computed tomography (CT) image, instead of the mammography image. In addition, the display layout setting unit 13 can also set, on the single screen of the monitor 17, a plurality of display regions for displaying a plurality of types of examination images captured in a plurality of types of examinations other than the ultrasound examination together with the ultrasound images.

As described above, a plurality of display regions for displaying the ultrasound image captured in the ultrasound examination of the same subject under examination and the examination image captured in an examination other than the ultrasound examination are set on the single screen of the monitor 17, so that the user can easily compare the ultrasound image with the examination image, and the image interpretation efficiency of the ultrasound image can be improved.

Figure 11:
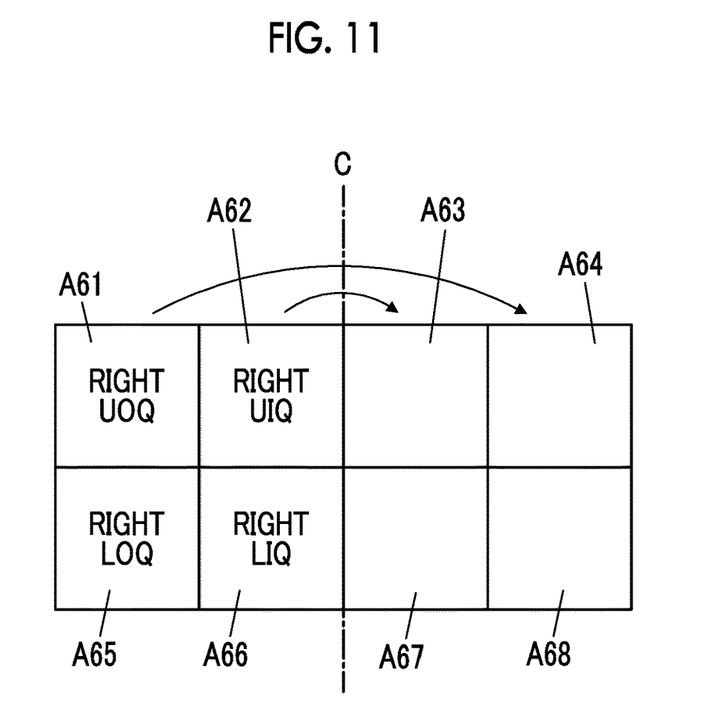
FIG. 11 is a diagram showing a state in which only display regions of the display layout, which correspond to a right-side breast, are set in Embodiment 1 of the present invention.

Further, for example, as shown in FIG. 11, the display layout setting unit 13 can set, among a plurality of display regions corresponding to both the left and right breasts of the subject under examination, a plurality of display regions corresponding to one breast based on the imaging positions read by the imaging position reading unit 14 or the user's instruction, and set a plurality of display regions corresponding to the other breast by reversing disposition of imaging positions corresponding to the set plurality of display regions.

In the example of FIG. 11, among eight display regions A61 to A68, in four display regions A61, A62, A65, and A66 located on the left side, corresponding imaging positions are set. The display region A61 corresponds to the UOQ imaging position of the right breast, the display region A62 corresponds to the UIQ imaging position of the right breast, the display region A65 corresponds to the LOQ imaging position of the right breast, and the display region A66 corresponds to the LIQ imaging position of the right breast.

In this case, for example, the display layout setting unit 13 sets the UOQ imaging position of the left breast in the display region A64 disposed at a position symmetric to the display region A61 with respect to a center line C, sets the UIQ imaging position of the left breast in the display region A63 disposed at a position symmetric to the display region A62 with respect to the center line C, sets the LOQ imaging position of the left breast in the display region A68 disposed at a position symmetric to the display region A65 with respect to the center line C, and sets the LIQ imaging position of the left breast in the display region A67 disposed at a position symmetric to the display region A66 with respect to the center line C. As a result, the display layout setting unit 13 can set the eight display regions A1 to A8 of the display layout L1 shown in FIG. 2 on the single screen of the monitor 17.

By setting the display layout in this manner, the input operation of the user can be simplified particularly in a case where the display layout is set based on the input operation of the user via the input device 19, and the user can perform the image interpretation more efficiently.

In addition, in the ultrasound examination of the subject under examination, there may be a case where a so-called B-mode image and a color image such as a so-called color Doppler image are captured as the ultrasound images. In this case, the display layout setting unit 13 can also set, for example, a plurality of display regions for displaying the B-mode image and the color image on the single screen of the monitor 17. As a result, the user can easily compare the B-mode image and the color image, which are captured at the same imaging position, so that the image interpretation efficiency of the ultrasound image can be improved.

In addition, for example, there may be a case where an ultrasound image corresponding to a part of the eight display regions A1 to A8 of the display layout L1 as shown in FIG. 2 is not captured. In this case, since there is a display region in which the ultrasound image is not disposed by the image disposition unit 15, for example, such a display region may be displayed as a blank in a case where the ultrasound image is displayed on the monitor 17. Even in this case as well, the user can intuitively grasp which imaging positions the ultrasound images displayed in the eight display regions A1 to A8 of the display layout L1 correspond to, and the image interpretation efficiency can be improved. Further, the user can intuitively grasp which position of the breast of the subject under examination is imaged and which position is not imaged.

Further, although not shown, the display device 1 can also comprise a plurality of monitors disposed adjacent to each other, instead of comprising one monitor 17. In this case, a single screen is formed by the plurality of monitors adjacent to each other, and the display layout setting unit 13 sets, on the single screen formed by the plurality of monitors adjacent to each other, a plurality of display regions of a display layout corresponding to a schematic diagram selected by the schematic diagram selection unit 12. As a result, the user can confirm a plurality of ultrasound images displayed on the larger single screen, so that the image interpretation efficiency can be further improved.

Further, in the description of the operation of the display device 1 using the flowchart of FIG. 5, the schematic diagram selection unit 12 selects the schematic diagram designated by the user in step S1, but it is also possible to continue to select the schematic diagram selected in the examination performed in the past even in a case where the schematic diagram is not newly selected by the user. This makes it possible for the user to eliminate the effort to designate the schematic diagram.

Embodiment 2

In Embodiment 1, a plurality of display regions of the display layout corresponding to the type of breast schematic diagram designated by the user are set, but it is also possible to set the plurality of display regions in consideration of the presence or absence of a finding at an examination portion of the subject under examination. Here, the finding refers to a suspicious portion where an abnormality such as a tumor has occurred in the breast of the subject under examination.

Figure 12:
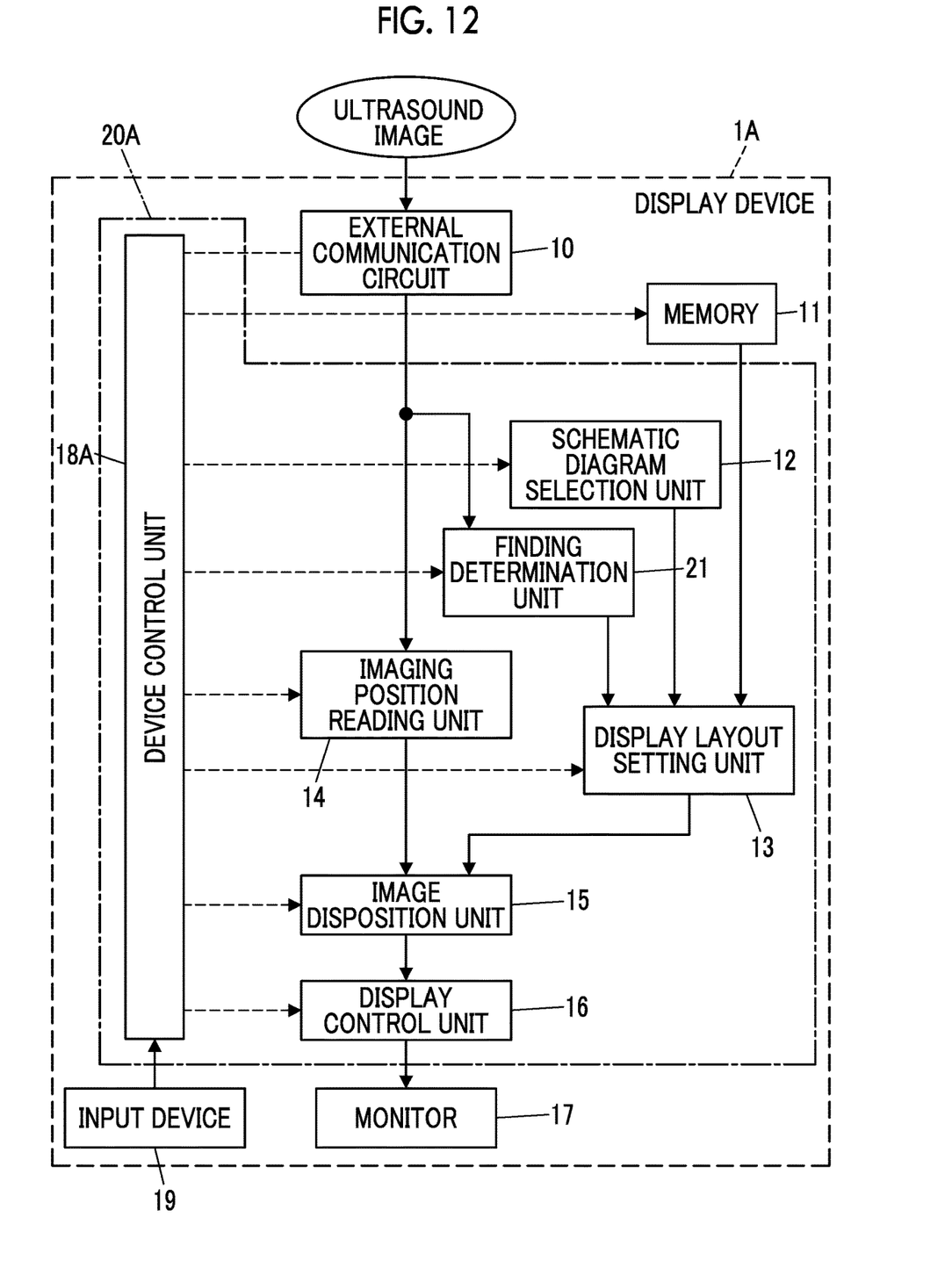
FIG. 12 is a block diagram showing a configuration of a display device according to Embodiment 2 of the present invention.

FIG. 12 shows a configuration of a display device 1A according to Embodiment 2.

In the display device 1A according to Embodiment 2, a finding determination unit 21 is added to the display device 1 of Embodiment 1 shown in FIG. 1, a device control unit 18A is provided instead of the device control unit 18, and a processor 20A including the finding determination unit 21 is provided instead of the processor 20. The finding determination unit 21 is connected to the display layout setting unit 13 and the device control unit 18A.

The finding determination unit 21 acquires the ultrasound image from the external ultrasound diagnostic apparatus (not shown), the external server device (not shown), or the like via the external communication circuit 10 and determines the presence or absence of the finding in the acquired ultrasound image.

The finding determination unit 21 can determine the presence or absence of the finding by, for example, performing image analysis on the ultrasound image and performing processing of recognizing the finding included in the ultrasound image. The finding determination unit 21 can determine the presence of the finding in a case where the finding is recognized in the ultrasound image, and can determine the absence of the finding in a case where the finding cannot be recognized in the ultrasound image.

The finding determination unit 21 can automatically recognize the finding in the ultrasound image by using, for example, a so-called computer-aided diagnosis (CAD) system. In addition, the finding determination unit 21 can automatically recognize the finding in the ultrasound image by using, for example, a method such as so-called machine learning.

In addition, in a case where a so-called annotation, a measurement line used for measuring the size or the like of the finding, or the like is attached to a portion corresponding to the finding in the ultrasound image, the finding determination unit 21 can also recognize the finding by extracting the annotation, the measurement line, or the like.

In addition, in a case where the finding is recognized in the ultrasound examination, a plurality of ultrasound images may be captured at an imaging position where the finding is recognized. In this case, the finding determination unit 21 can determine the presence of the finding in a case where a plurality of ultrasound images captured at one imaging position are input from the external ultrasound diagnostic apparatus (not shown) or the external server device (not shown), and can determine the absence of the finding in a case where no more than one ultrasound image captured at one imaging position is input.

Here, examples of the combination of the plurality of ultrasound images captured at one imaging position include a combination consisting of a B-mode image and an ultrasound image of a type other than the B-mode image, such as a so-called Doppler image and a so-called elastic image, and a combination consisting of a plurality of ultrasound images captured at the same imaging position by changing the direction of the ultrasound probe.

In addition, the plurality of ultrasound images captured at one imaging position also include a plurality of ultrasound images obtained by imaging the same site of the subject under examination with slight shift in the imaging position.

In addition, in a case where the finding is recognized in the ultrasound examination, an examination image may be captured in an examination other than the ultrasound examination at an imaging position where the finding is recognized. In this case, the finding determination unit 21 can determine the presence of the finding in a case where the examination image other than the ultrasound image is input from an external examination device (not shown), the external server device (not shown), or the like, and can determine the absence of the finding in a case where only the ultrasound image is input.

In this way, information on the determination result with or without the finding by the finding determination unit 21 is transmitted to the display layout setting unit 13.

Similarly to Embodiment 1, the display layout setting unit 13 sets, on the single screen of the monitor 17, a plurality of display regions of a display layout corresponding to the breast schematic diagram selected by the schematic diagram selection unit 12 in a case where the finding determination unit 21 has determined the absence of the finding.

Figure 13:
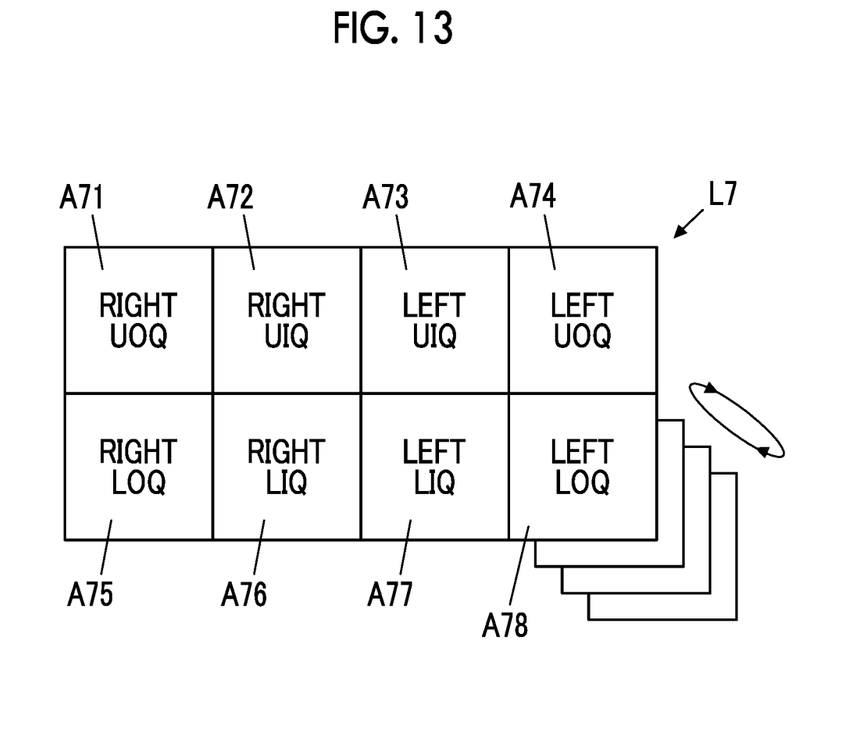
FIG. 13 is a diagram showing an example of a display layout in a case where presence of a finding is determined in Embodiment 2 of the present invention.

In addition, the display layout setting unit 13 sets, in a case where the finding determination unit 21 has determined the presence of the finding, a plurality of display regions of a display layout different from those in a case where it is determined as the absence of the finding, on the single screen of the monitor 17. For example, as shown in FIG. 13, the display layout setting unit 13 can set eight display regions A71 to A78 of a display layout L7 such that, in the display region A78 corresponding to an imaging position where the finding is recognized among the display regions A71 to A78, a plurality of ultrasound images captured at the imaging position and an examination image other than the ultrasound image are switched and displayed in response to an input operation of the user via the input device 19.

Figure 14:
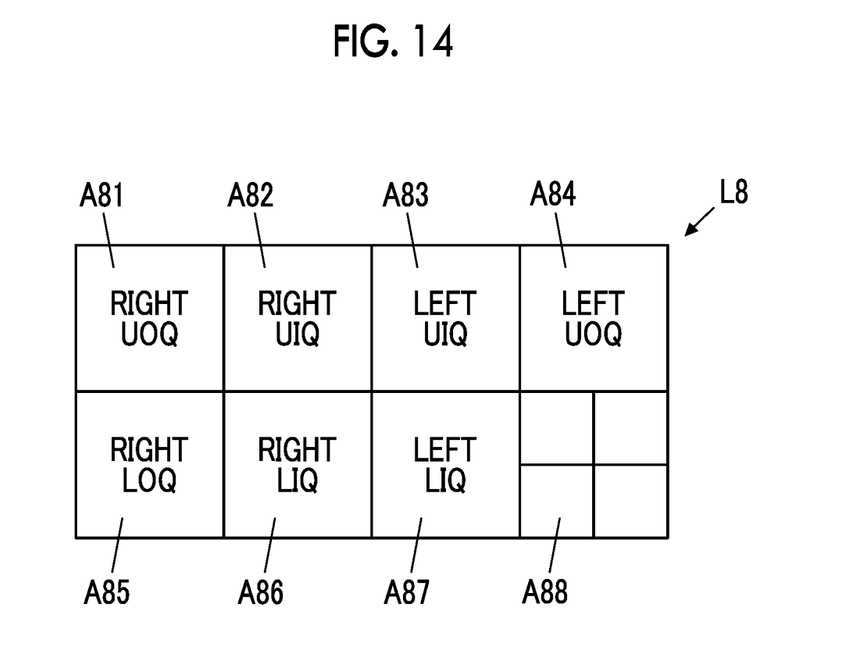
FIG. 14 is a diagram showing another example of the display layout in a case where the presence of the finding is determined in Embodiment 2 of the present invention.

In addition, for example, as shown in FIG. 14, the display layout setting unit 13 can set eight display regions A81 to A88 of a display layout L8 such that, in the display region A88 corresponding to an imaging position where the finding is recognized among the display regions A81 to A88, a plurality of ultrasound images captured at the imaging position and an examination image other than the ultrasound image are arranged and displayed.

Further, although not shown, the display layout setting unit 13 can set, on the single screen of the monitor 17, for example, a plurality of display regions of a first display layout which is similar to a case where it is determined as the absence of the finding except that a representative single ultrasound image is set to be disposed in a display region corresponding to the imaging position where the finding is recognized, and can further set, on the single screen of the monitor 17, a plurality of display regions of a second display layout in which other ultrasound images captured at the imaging position where the finding is recognized and the examination image other than the ultrasound image are arranged and displayed. In this case, after the ultrasound image disposed in the first display layout is displayed on the monitor 17, the ultrasound images and the examination image other than the ultrasound image, which are disposed in the plurality of display regions of the second display layout, can be displayed in response to an input operation of the user via the input device 19.

From the above, with the display device 1A according to Embodiment 2 of the present invention, since the presence or absence of the finding in the ultrasound image is determined by the finding determination unit 21, and a plurality of display regions of different display layouts depending on the presence or absence of the finding are set on the single screen by the display layout setting unit 13, the user can not only intuitively grasp which the plurality of ultrasound images displayed on the monitor 17 correspond to which imaging positions, but also easily confirm the ultrasound image including the finding or the examination image, which makes it possible to improve the image interpretation efficiency.

EXPLANATION OF REFERENCES 1, 1A: display device
11: memory
12: schematic diagram selection unit
13: display layout setting unit
14: imaging position reading unit
15: image disposition unit
16: display control unit
17: monitor
18, 18A: device control unit
19: input device
20A: processor
A1 to A8, A11 to A19, A21 to A24, A31 to A34, A41 to A48, A51 to A56, A61 to A68,
A71 to A78, A81 to A88: display region
C: center line
L1 to L8: display layout
P1: protrusion
PM: probe mark
S: schema image
U: ultrasound image

What is claimed is:

1. A display device comprising:
one or a plurality of adjacent monitors configured to form a single screen;
a memory configured to store a plurality of display layouts each of which has a plurality of display regions for displaying a plurality of ultrasound images on the single screen; and
a processor configured to
select, from among a plurality of schematic diagrams each of which divides a breast of a subject under examination into a plurality of regions, one schematic diagram based on a user's designation,
set, on the single screen, a plurality of display regions of a display layout corresponding to the schematic diagram selected,
read imaging positions of the ultrasound images from the ultrasound images, and
dispose the ultrasound images in the display regions which are set, based on the imaging positions which are read.

2. The display device according to claim 1, wherein the processor is further configured to set, on the single screen, a plurality of display regions disposed at positions corresponding to a plurality of regions in the schematic diagram which is selected.

3. The display device according to claim 1, wherein the processor is further configured to change the plurality of display regions already set on the single screen, based on the user's instruction.

4. The display device according to claim 1, wherein the processor is further configured to
determine presence or absence of a finding in the ultrasound image,
set, on the single screen, a plurality of display regions of different display layouts, corresponding to a determination result of the presence of the finding and a determination result of the absence of the finding.

5. The display device according to claim 1, wherein the processor is further configured to set, on the single screen, a plurality of display regions for arranging and displaying an ultrasound image captured in a latest examination performed on the same subject under examination and an ultrasound image captured in a past examination, based on the user's instruction.

6. The display device according to claim 1, wherein the processor is further configured to set, on the single screen, a plurality of display regions for arranging and displaying an ultrasound image captured in an examination performed on the same subject under examination and an examination image acquired in an examination other than an ultrasound examination, based on the user's instruction.

7. The display device according to claim 1, wherein the processor is further configured to set, among a plurality of display regions corresponding to both left and right breasts of the subject under examination, a plurality of display regions corresponding to one breast based on the imaging positions which are read or the user's instruction, and sets a plurality of display regions corresponding to the other breast by reversing disposition of imaging positions corresponding to the set plurality of display regions.

8. The display device according to claim 1, wherein the processor is further configured to set, on the single screen, a plurality of display regions for arranging and displaying a B-mode image and a color image captured in an ultrasound examination performed on the same subject under examination, based on the user's instruction.

9. The display device according to claim 1, wherein the processor is configured to read the imaging position of the ultrasound image by analyzing a schema image that is superimposed and displayed on the ultrasound image and that indicates a position of an ultrasound probe during imaging with respect to the breast.

10. The display device according to claim 1,
wherein the processor is further configured to read the imaging position of the ultrasound image based on a position of an ultrasound probe, which is written in a tag accompanying the ultrasound image.

11. A control method of a display device, comprising:
causing a memory to store a plurality of display layouts each of which has a plurality of display regions for displaying a plurality of ultrasound images on a single screen formed by one or a plurality of adjacent monitors;
selecting, from among a plurality of schematic diagrams each of which divides a breast of a subject under examination into a plurality of regions, one schematic diagram based on a user's designation;
setting, on the single screen, a plurality of display regions of a display layout corresponding to the selected schematic diagram;
reading imaging positions of the ultrasound images from the ultrasound images; and
disposing the ultrasound images in the set display regions based on the read imaging positions.

12. The control method of a display device according to claim 11,
wherein a plurality of display regions disposed at positions corresponding to a plurality of regions in the schematic diagram selected based on the user's designation are set on the single screen.

13. The control method of a display device according to claim 11,
wherein the plurality of display regions already set on the single screen are changed based on the user's instruction.

14. The control method of a display device according to claim 11, further comprising:
determining presence or absence of a finding in the ultrasound image;
setting a plurality of display regions of different display layouts corresponding to a determination result of the presence of the finding and a determination result of the absence of the finding on the single screen.

15. The control method of a display device according to claim 11,
wherein a plurality of display regions for arranging and displaying an ultrasound image captured in a latest examination performed on the same subject under examination and an ultrasound image captured in a past examination are set on the single screen based on the user's instruction.

16. The control method of a display device according to claim 11,
wherein a plurality of display regions for arranging and displaying an ultrasound image captured in an examination performed on the same subject under examination and an examination image acquired in an examination other than an ultrasound examination are set on the single screen based on the user's instruction.

17. The control method of a display device according to claim 11,
wherein, among a plurality of display regions corresponding to both left and right breasts of the subject under examination, a plurality of display regions corresponding to one breast are set based on the read imaging positions or the user's instruction, and a plurality of display regions corresponding to the other breast are set by reversing disposition of imaging positions corresponding to the set plurality of display regions.

18. The control method of a display device according to claim 11,
wherein a plurality of display regions for arranging and displaying a B-mode image and a color image captured in an ultrasound examination performed on the same subject under examination are set on the single screen based on the user's instruction.

19. The control method of a display device according to claim 11,
wherein the imaging position of the ultrasound image is read by analyzing a schema image that is superimposed and displayed on the ultrasound image and that indicates a position of an ultrasound probe during imaging with respect to the breast.

20. The control method of a display device according to claim 11,
wherein the imaging position of the ultrasound image is read based on a position of an ultrasound probe, which is written in a tag accompanying the ultrasound image.

* * * * *